(12) United States Patent
Busch, Jr. et al.

(10) Patent No.: US 6,627,181 B1
(45) Date of Patent: Sep. 30, 2003

(54) SINGLE AND MULTI LAYERED NAIL LACQUERS

(75) Inventors: Francis Busch, Jr., Southbury, CT (US); Jack S. Wooster, Stratford, CT (US)

(73) Assignee: Pro Strong INC, Oakville, CT (US)

( * ) Notice: Subject to any disclaimer, the term of this patent is extended or adjusted under 35 U.S.C. 154(b) by 110 days.

(21) Appl. No.: 09/694,215

(22) Filed: Oct. 23, 2000

(51) Int. Cl.[7] ............... A61K 6/00; A61K 7/00; A61K 7/04
(52) U.S. Cl. .................... 424/61; 424/401
(58) Field of Search ............... 424/400, 401, 424/61

(56) References Cited

U.S. PATENT DOCUMENTS 5,093,108 A * 3/1992 Pappas et al. ............ 424/61
5,330,750 A * 7/1994 Sheard et al. ............ 424/61

* cited by examiner

Primary Examiner—Thurman K. Page
Assistant Examiner—S. Howard

(57) ABSTRACT

An enamel base coat layer and a nail repair and adhesive layer are contained as a two layered solution in a single nail polish type bottle. The nail repairing and strengthening layer is the lower layer has both higher viscosity and higher specific gravity than the upper layer.

2 Claims, 1 Drawing Sheet

SINGLE AND MULTI LAYERED NAIL LACQUERS

BACKGROUND OF THE INVENTION

As is well known in the art, a plasticized nitrocellulose base lacquer is ordinarily applied to a finger nail or a toe nail as a basecoat prior to the application of typical pigmented nail enamel. The primary function of the base coat is to provide adhesion between the nail and the pigmented nail enamels used for decorative purposes. However, many users of nail enamel suffer with nails that are damaged, very thin and soft Occasionally the nail may have slight tears or may have separation between the several layers of the normal nail. Repair of these defects ordinarily requires the use of a separate more adhesive type produce The present invention is directed toward new produces and processes which provide enhanced repair and subsequent base coat enamels for damaged nails.

SUMMARY OF THE INVENTION

In accordance with the principles of this invention, a new and improved nail lacquer repair adhesive layer is applied to a damaged nail and repairs it. This new layer is both heavier and has higher viscosity than prior art layers. In particular, this new layer has a specific gravity falling within the range of 0.950 and 1.10 grams per cubic centimeter and a viscosity falling within the range of 500 and 3000 centipoise. Other than these unique characteristics of higher viscosity and higher density, the new layer contains well known and commonly used components, ie, a primary film forming ingredient, a supplemental film forming resin, plasticizers, and organic solvents for the film formers, resin and plasticizers.

The invention also employs an enamel base coat layer containing the same well known and commonly used components as the adhesive layer, but is characterized by both lower specific gravity and lower viscosity. In particular, this base coat layer has a specific gravity falling within the range of 0.700 and 0.950 grams per cubic centimeter and a viscosity falling within the range of 50 and 700 centipoise The current invention provides both the ability to repair a damaged fingernail and a superior basecoat using a separate application first of the adhesive layer and secondly of the base coat layer. These applications can be made by a conventional nail enamel brush disposed in a single bottle. More particularly these two products are disposed as separate layers in this bottle. The more viscous layer with the higher specific gravity settles to the bottom of the bottle while the lighter less viscous solution rises to the top.

When the heavier more viscous bottom layer is filled first and the lighter less viscous top layer is filled second, the heavier layer settles on the bottom half of the bottle. The lighter layer will float and rest on top of the heavier more viscous bottom layer. When the brush is inserted it will extend into the bottom layer. When the brush is withdrawn from the bottle without mixing, the denser more viscous bottom layer clings to the brush and can be applied to the area of the nail-requiring repair. When no repair is required and the product is used as a base coat, both layers are mixed together and easily applied with the same brush. The adhesive nature of the bottom layer even when diluted by mixing with lower viscosity top layer provide a basecoat which provides outstanding adhesion between the nail and pigmented decorative enamels.

After the product is mixed and used as a basecoat and allowed to stand overnight in an upright position, the heavier more viscous solution settles back to lower half of the bottle while the lighter less viscous layer again rises to the top and is again ready for use either as a repair for damaged nails or can be re-mixed and used as a basecoat.

The separation of the two layers after mixing is accelerated when small particle size pigments are included in the heavier more viscous bottom layer. These small particle size pigments may either be an ultra-fine grade of titanium dioxide or ultra-fine zinc oxide. Both pigments are well known in the art of producing sun-blocking products. They are not typically used in nail enamels because of their low refractive index. While they are opaque in solution, they are transparent in dry film form.

This translucence is an advantage for formulating products of the current invention because base costs and fingernail repair adhesives are transparent as highly pigmented material would often dash with the colors of the pigmented nail enamels which may follow.

BRIEF DESCRIPTION OF THE DRAWING

The single

DETAILED DESCRIPTION OF SPECIFIC EXAMPLES

Figure 1:
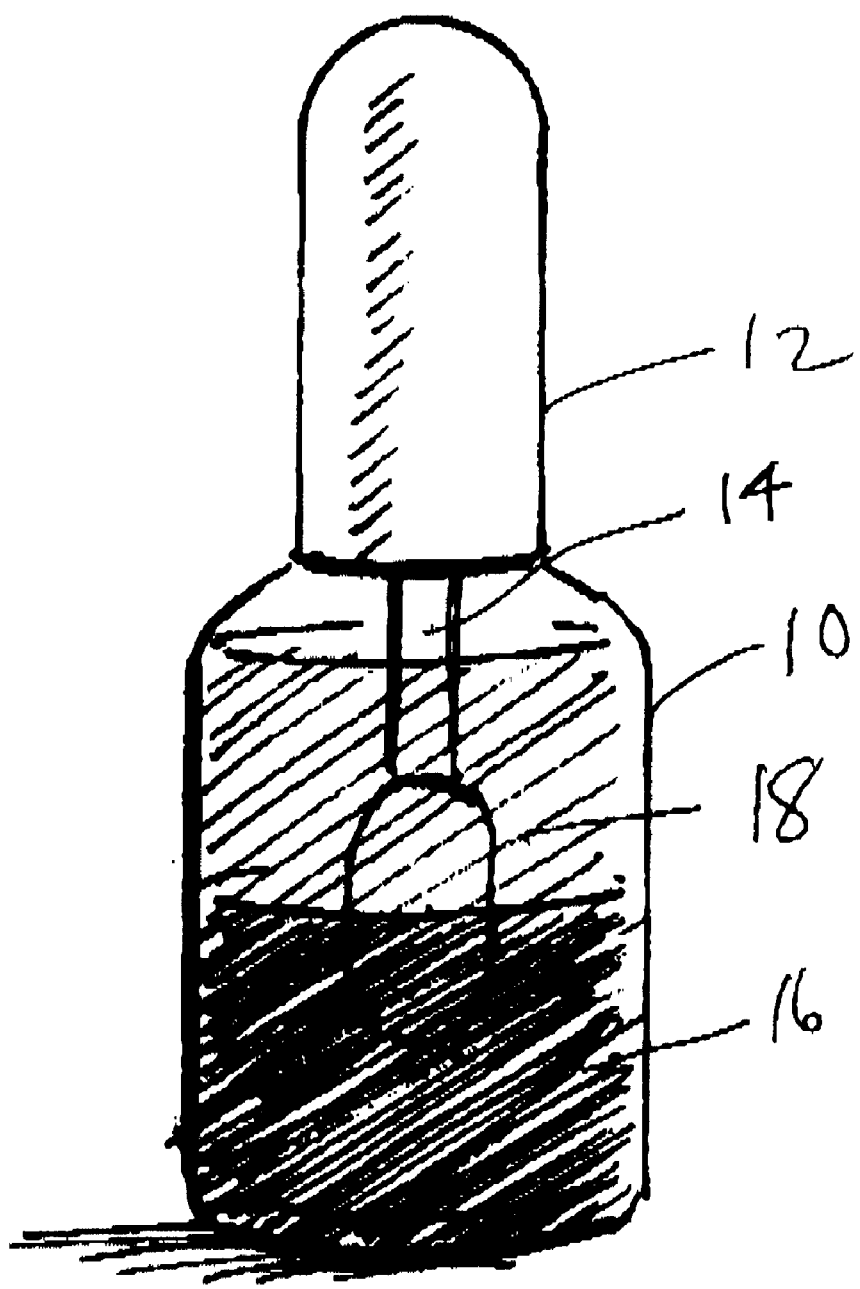
FIG. 1 illustrates a known conventional nail enamel bottle 10 having a removable cap 12. A nail enamel brush 14 is secured to the cap. The bottle contains the heavier more viscous nail lacquer repair layer as a bottom layer 16 and the lighter less viscous enamel base coat layer 18, the brush as inserted extends into the bottom layer. The use of this bottle, brush and layers is as described above.

The upper layer lacquers of this invention exhibit a use viscosity of between about 50 cps to about 700 cps as measured with a standard Brookfield Viscometer model LVT and a spindle and RPM chosen appropriate for the lacquer being measured as is well known in the art. Further, the upper layer lacquers of this invention have a specific gravity between 0.70 g/cubic centimeter and 0.95 gram per cubic centimeter as measured with a standard weight per gallon cup using the American Society for Testing Materials method D 1475.

The bottom layer lacquers of this invention have a use viscosity of between 750 cps. And 3000 cps when measured as above.

The actual viscosity and specific gravity of the top layer are adjusted so that the bottom layer is more viscous and with a higher specific gravity.

Example 1 is a top layer lacquer of this invention. It has a viscosity of 500 cps. and specific gravity of 0.890 when measured as described above. It uses nail enamel ingredients well known in the art. Both the viscosity and the specific gravity of this top layer can be easily adjusted either higher or lower. If the viscosity is too high, a small addition of any of the solvents will lower the viscosity. Such an adjustment is well known in the art. If either viscosity or specific gravity is too low, more film forming polymer or modifying resin is added until properties are within the proper range. Making such an adjustment is well known in the art of lacquer manufacture.

Example 1 Formula Top Layer

| | Ingredient | Parts by Weight |
|---|---|---|
| Solvents: | Ethyl Acetate | 15 |
| | Butyl Acetate | 25 |
| | Propyl Acetate | 5 |
| Diluents: | Heptane | 18 |
| | Isopropyl alcohol | 6.5 |
| Film Forming Polymer | Nitrocellulose ½ Second ISO propyl alcohol wet | 15 |
| Modifying Resin | Polyester Resin | 6.0 |
| Plasticizer | Dibutyl Phthalate | 4.0 |
| | Camphor | 2.0 |
| | TriPhenyl Phosphate | 3.5 |
| Tinting Color | Violet 2 | QS |

The polyester resin used in this example has the chemical name AdipicAcid/Neopentyl Glycol/Trimellitic Anhydride Copolymer. All the ingredients used in this example are well known in the art.

Example 1 bottom layer which follows has a viscosity of 2000 cps. And a specific gravity of 0.970.

Example 1 Formula bottom Layer

| | Ingredient | Parts by Weight |
|---|---|---|
| Solvents: | Ethyl Acetate | 13 |
| | Butyl Acetate | 23 |
| | Propyl Acetate | 5 |
| Diluents: | Heptane | 13 |
| | Isopropyl alcohol | 9.5 |
| Film Forming Polymer | Nitrocellulose ½ Second Iso propyl alcohol wet | 10.5 |
| | Nitrocellulose 5–6 second Grade Isopropyl alcohol Wet | 0.5 |
| Modifying Resin | Polyester Resin | 6.0 |
| Plasticizer | Dibutyl Phthalate | 4.0 |
| | Camphor | 2.0 |
| | TriPhenyl Phosphate | 3.5 |
| Tinting Color | Red 33 | Q.S |

The above lacquers were manufactured in an explosion proof facility consistent with good manufacturing practices all well known in the art of nail polish manufacture. The lacquers of the above example fell within the ranges required for maintaince of separation as stated above.

RESULTS

Into a standard ½ ounce nail polish 6.5 grams of the example 1 bottom layer were filled. Additionally 6.5 grams of example 1 top layer lacquer were filled and a brush Assembly added. The brush extends into the lower half of the bottle and rest in the lower half lacquer. Bottles so filled were given to subjects with either peeling nails or weak nails with edges broken. Subject were instructed to use the product without mixing to glue the defected parts of the nail together. Because of the high viscosity of the lower layer, it remained on the brush when the brush was withdrawn from the bottle and subjects could easily mend the broken portions of the nail back together. Subjects were then instructed to mix the two layers together by gently shaking the bottles until the two layers were uniformly combined. When this was accomplished subjects were instructed to apply the mixed layers to the nail with the same brush as a base coat for pigmented nail enamel of commerce. The panelist then were ask to wear the polish for one week and report how the base coat of this invention performed at maintaining the adhesion between the nail and the pigmented nail enamel of commerce. This test was performed with 20 subjects. All reported that the base coat of this invention either out performed the basecoat they currently use or were equivalent.

The samples that were mixed as just described were then allowed to stand in an upright position where they were observed for the time required for the two layers to separate into their original upper and lower positions. After four days all of the samples were separated to the degree that they would be used either as a nail adhesive or re-mixed and used as a base coat.

When an ultrafine pigment such as titanium dioxides and zinc oxide is used in the bottom layer the time required for separation of the two layers is reduced. There are two examples of the bottom layer containing ultra flue pigments using titanium dioxide as the pigment.

Bottom Layer Containing Ultra fine Pigments

| | Ingredient | Examples 2 and 3 Parts by Weight | |
|---|---|---|---|
| Solvents: | Ethyl Acetate | 13 | 13 |
| | Butyl Acetate | 23 | 23 |
| | Propyl Acetate | 5 | 5 |
| Diluents: | Heptane | 12.9 | 11.9 |
| | Isopropyl alcohol | 9.5 | 9.5 |
| Film Forming Polymer | Nitrocellulose ½ Second Iso propyl alcohol wet | 10.5 | 10.5 |
| | Nitrocellulose 5–6 second Grade Isopropyl alcohol Wet | 10.5 | 10.5 |
| Modifying Resin | Polyester Resin | 6.0 | 6.0 |
| Plasticizer | Dibutyl Phthalate | 4.0 | 4.0 |
| | Camphor | 2.0 | 2.0 |
| | TriPhenyl Phosphate | 3.5 | 3.5 |
| Tinting Color | Red 33 | Q.S | Q.S |
| Ultrafine Titanium Dioxide .2 micron average particle size | | .10 | 1.0 |

When the above example 2 and 3 bottom layers were used with the top layer cited above the viscosity of these bottom layer was 2000 cps and 2050 cps respectively. The specific gravities measured 0.99 and 1.06 grams per cubic centimeter respectively. Two further examples were prepared where the ultrafine titanium dioxide was replaced part for part with ultra fine zinc oxide with an average particle size less than 0.2 micron. The viscosity and specific gravitates were 2100 and 2300 cps. respectively. The specific gravities were 1.01 and 1.04 respectively. While both pigmented bottom layers are opaque in the bottle, they remain for the most part translucent on the nail. When multifunctional multilayered products are prepared using the bottom layers of examples 2,3,4,and 5 instead of bottom layer of example one, all performed both as a repair adhesive when used with out mixing and superior basecoat after mixing. The examples, which included ultra fine titanium dioxide or ultra fine zinc oxide, had the advantage of separating back into two distinct layers after mixing. The time for separation was reduced from about 4 days for examples 1 to over night with examples 2,3,4,and 5.

Both the ultrafine titanium dioxide and zinc oxide are widely commercially available. The zinc oxide can be purchased from BASF Aktirngelellschaft, Fine Chemicals Division, Ludwigshafen under the trade name Z COTE. The ultra fine titanium dioxide is also widely available. Cardre Inc. South Plainfield N.J. is a source. Their trade name is 70170 UFTio2.

While the invention has been described with detailed reference to examples and drawing, the protection solicited is to be limited only by the terms of the claims which follow.

What is claimed is:

1. A nail lacquer repair adhesive layer having a specific gravity falling within the range of 0.950 and 1.10 grams per cubic centimeter and a viscosity falling within the range of 500 and 3000 centipoise and containing a primary film forming ingredient; a supplemental film forming resin, plasticizers; organic solvents for the primary ingredient and the supplemental film forming resin and plasticizers; and 0.02 to 1.00 parts per weight of ultra fine pigment particles having a size less than 0.2 microns, said layer containing a tinting color.

2. A nail lacquer repair adhesive layer having a specific gravity falling within the range of 0.950 and 1.10 grams per cubic centimeter and a viscosity falling within the range of 500 and 3000 centipoise and containing a primary film forming ingredient; a supplemental film forming resin, plasticizers; organic solvents for the primary ingredient and the supplemental film forming resin and plasticizers; and 0.02 to 1.00 parts per weight of ultra fine pigment particles having a size less than 0.2 microns, said particles being selected from the group consisting of zinc oxide and titanium oxide.

* * * * *